United States Patent [19]

Blumbach et al.

[11] 4,293,550
[45] Oct. 6, 1981

[54] CEPHALOSPORIN DERIVATIVES

[75] Inventors: Jürgen Blumbach, Frankfurt am Main; Walter Dürckheimer, Hattersheim am Main; Elmar Schrinner, Wiesbaden, all of Fed. Rep. of Germany

[73] Assignee: Hoechst Aktiengesellschaft, Frankfurt am Main, Fed. Rep. of Germany

[21] Appl. No.: 971,558

[22] Filed: Dec. 20, 1978

[30] Foreign Application Priority Data

Dec. 24, 1977 [DE] Fed. Rep. of Germany ....... 2758001

[51] Int. Cl.³ .................. A61K 31/545; C07D 501/34
[52] U.S. Cl. ....................................... 424/246; 544/28; 548/194
[58] Field of Search ...................... 544/27, 28; 424/246

[56] References Cited

U.S. PATENT DOCUMENTS 4,092,474  5/1978  Yoshioka et al. .................. 424/246
4,098,888  7/1978  Ochiai et al. ....................... 544/27
4,152,432  5/1979  Heymes et al. .................... 424/246

FOREIGN PATENT DOCUMENTS 2556736  6/1975  Fed. Rep. of Germany .

*Primary Examiner*—Paul M. Coughlan, Jr.
*Attorney, Agent, or Firm*—Curtis, Morris & Safford

[57] ABSTRACT

Cephalosporin derivatives of the formula

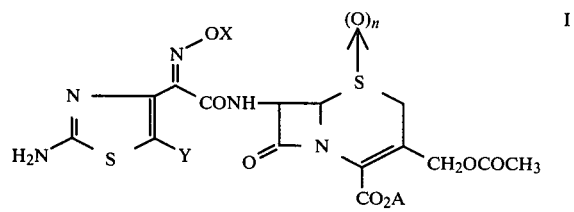

processes for their manufacture and their use for combating bacterial infections.

5 Claims, No Drawings

CEPHALOSPORIN DERIVATIVES

The invention relates to cephalosporin derivatives of the general formula I

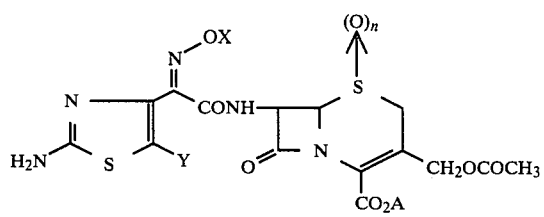

in which n can denote 0 or 1 and X represents hydrogen, optionally substituted alkyl with 1 to 4 C atoms, optionally substituted carboxymethyl, which can also be present in the form of its physiologically acceptable salts, optionally substituted alkoxycarbonyl-methyl with 1 to 4 C atoms in the alkyl part, optionally substituted aminocarbonylmethyl or optionally substituted cyanomethyl, Y represents methyl or halogen and A represents hydrogen, an ester radical which can be easily split off or a physiologically acceptable cation.

If X represents alkyl with 1 to 4 atoms, the radicals methyl, ethyl, propyl and butyl, preferably methyl, which can also be substituted, for example by halogen, in particular bromine or chlorine, by hydroxyl or by amino, which can also be monosubstituted or disubstituted, for example by alkyl with 1 to 4 C atoms, may be mentioned in particular.

If X represents alkoxycarbonyl with 1 to 4 C atoms in the alkyl part, possible radicals are, in particular, methoxycarbonylmethyl and ethoxycarbonylmethyl.

X in the above meaning of carboxymethyl, which can also be present in the form of its physiologically acceptable salts, alkoxycarbonylmethyl, aminocarbonylmethyl and cyanomethyl can be monosubstituted or disubstituted in the methylene group, for example by alkyl with 1 to 4 C atoms, preferably methyl, it also being possible, in particular, for 2 alkyl substituents to be closed to form a 3-membered to 6-membered carbocyclic ring.

In detail, particularly preferred radicals X which may be mentioned are hydrogen, methyl, ethyl, n-propyl, isopropyl, n-butyl, iso-butyl, carboxymethyl, methoxycarbonylmethyl, ethoxycarbonylmethyl, aminocarbonylmethyl and cyanomethyl.

Methyl, bromine, chlorine and fluorine are preferred for Y, but chlorine and fluorine are particularly preferred.

The tert.-butyl ester and trimethylsilyl ester, and also the benzyl, benzhydryl, trichloroethyl, benzoylmethyl, methoxymethyl or p-methoxybenzyl ester may be mentioned as preferred esters, in the meaning of A, which can be easily split off.

Examples of physiologically acceptable cations A which may be mentioned are an alkali metal ion, in particular the sodium ion and potassium ion, an alkaline earth metal ion, in particular the calcium ion and magnesium ion, and the ammonium ion, but preferably a sodium ion, as well as an optionally substituted alkylated ammonium ion, such as, preferably, triethylammonium, diethylammonium, dimethylammonium or morpholinium, benzylammonium, procainium, L-argininium and L-lysinium. Corresponding physiologically acceptable cations are also possible in the case where X is present in the form of a salt of the carboxymethyl group.

The hydroximino or alkoximino group in the compounds of the general formula I, II, IV and V can be present in the syn form and also in the anti form, but particularly preferably in the syn form. The designation syn or anti expresses the spatial position relative to the carboxamide group in the compounds I and III, to the carboxyl group in the compounds III and to the alkoxycarbonyl group in the compounds V, the syn position being that position in which the OX group is on the same side of the C=N double bond as the carboxamide, carboxyl or alkoxycarbonyl group.

2-Aminothiazoles of the general formula I, III, IV and V can each exist in two tautomeric forms, which can be present together in an equilibrium state and can be represented by the following equilibrium equations.

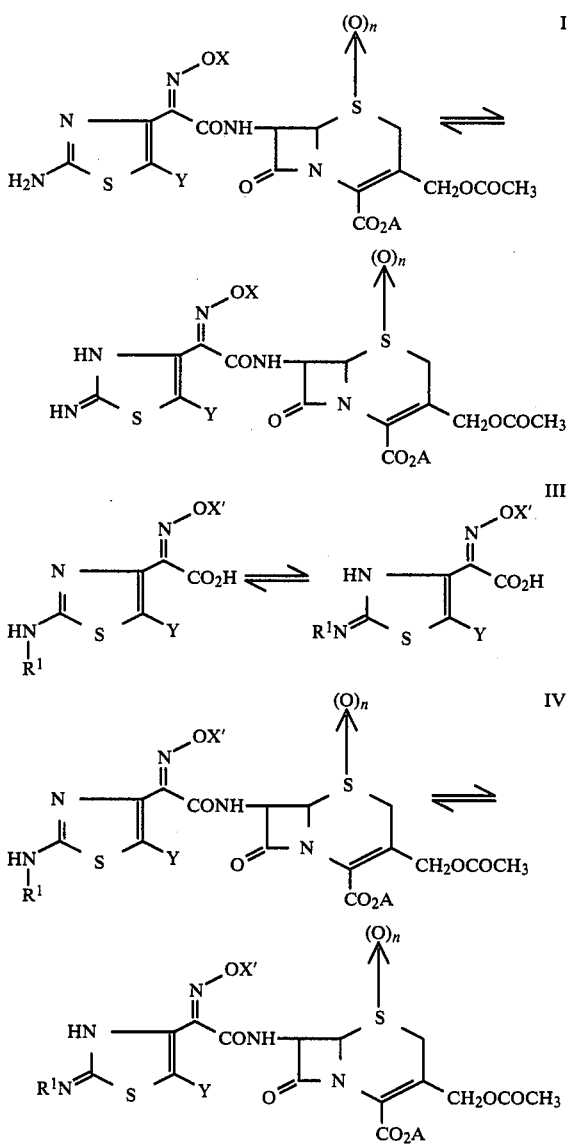

-continued

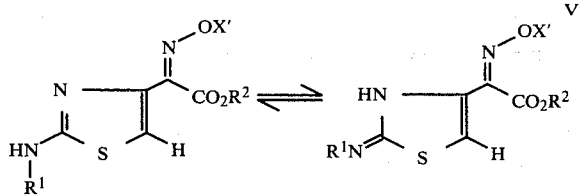

In the present documents, when formulae are represented, the two tautomers are not given in every case. For reasons of expediency, the formulae are restricted to the representation of the amino-thiazole tautomer

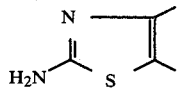

to which the nomenclature of the compounds also relates.

The invention furthermore relates to a process for the manufacture of cephem compounds of the general formula I, which comprises reacting lactams of the general formula II

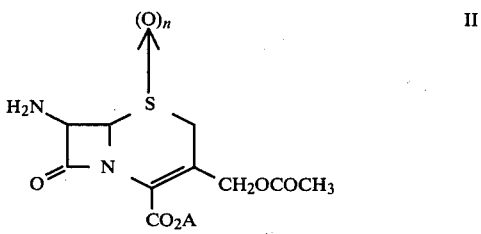

in which A and n have the meanings indicated above, with a carboxylic acid of the general formula III

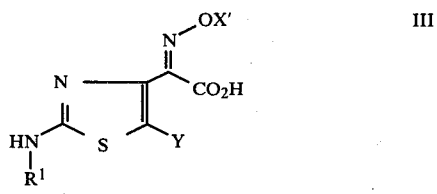

or an activated derivative thereof, to give a compound of the general formula IV

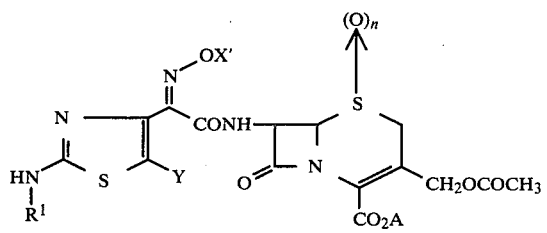

and
(a) optionally oxidizing the resulting product on the sulfer of the cephem ring to give the R- or S-sulfoxide, and/or
(b) splitting off a radical $R^1$ in the meaning of a protective group, and/or
(c) converting the radical X', if it does not denote X, into the radical X.

In the formulae III and IV, $R^1$ represents hydrogen, or represents an amino-protective group which is known from peptide chemistry, such as, for example, optionally substituted alkyl, such as, preferably, tert.-butyl, tert.-amyl, benzyl, p-methoxybenzyl, benzhydryl, trityl and phenylethyl, optionally substituted aliphatic acyl, such as, for example, formyl, chloroacetyl, bromoacetyl, trichloroacetyl and trifluoroacetyl, or optionally substituted alkoxycarbonyl, such as, for example, trichloroethoxycarbonyl or benzyloxycarbonyl and X' represents X, or represents a group which can be easily split off, such as, for example, formyl, trifluoroacetyl, chloroacetyl, bromoacetyl, trityl, tert.-amyl, tert.-butyl, benzhydryl and tetrahydropyranyl, but preferably represents tert.-butyl, trityl and tetrahydropyranyl, or represents a group of the formula $-CH_2CO_2R^3$, in which $R^3$ denotes a radical which can be split off under mild conditions, such as, preferably, trichloroethyl, tert.-butyl, benzyl, p-methoxyphenyl, benzhydryl or trityl.

Suitable activated derivatives of the carboxylic acids of the general formula III are, in particular, the halides, preferably chlorides and bromides, and furthermore the anhydrides and mixed anhydrides, the azides and activated esters, preferably those with p-nitrophenol, 2,4-dinitrophenol, methylene-cyanohydrin, N-hydroxysuccinimide and N-hydroxyphthalimide, and particularly preferably with 1-hydroxybenzotriazole and 6-chloro-1-H-hydroxybenzotriazole. Suitable mixed anhydrides are, in particular, those with lower alkanoic acids, for example with acetic acid and particularly preferably with substituted acetic acids, such as, for example, trichloroacetic acid, pivalic acid or cyanoacetic acid. However, the mixed anhydrides with carbonic acid half-esters, which are obtained, for example, by reacting the carboxylic acids III, in which $R^1$ does not denote hydrogen, with benzyl, p-nitrobenzyl, iso-butyl, ethyl or allyl chloroformate, are also particularly suitable. The activated derivatives can be reacted as isolated substances or in situ.

In general, the cephem derivatives II are reacted with the carboxylic acid III, or an activated derivative thereof, in the presence of an inert solvent. Particularly suitable solvents are chlorinated hydrocarbons, such as, preferably, methylene chloride and chloroform; ethers, such as, for example, diethyl ether and, preferably, tetrahydrofuran and dioxan; ketones, such as, preferably, acetone and butanone; amides, such as, preferably, dimethylformamide and dimethylacetamide, or water. It can also prove advantageous to use mixtures of the solvents mentioned. This is frequently the case when the cephem compound II is reacted with an activated derivative of the carboxylic acid III which has been produced in situ.

The reaction of cephem compounds II with carboxylic acids III, or activated derivatives thereof, can be carried out in a temperature range from about $-50°$ to about $+80°$ C., preferably between $-20°$ and $+50°$ C., but particularly preferably between $-20°$ and room temperature.

The reaction time depends on the reactants, the temperature and the solvent or solvent mixture and is usually between about ¼ and about 72 hours.

In individual cases it can also prove advantageous to react the free carboxylic acid of the formula III directly with a cephem compound of the formula II in which A denotes an ester radical which can be easily split off, such as, preferably, tert.-butyl or trimethylsilyl, and n can be 0 and 1, a water-binding agent being advantageously added in an approximately equimolar amount. Examples of possible water-binding agents are carbodiimides, in particular dicyclohexylcarbodiimide. This reaction is carried out in inert solvents, such as, preferably, methylene chloride, dimethylformamide, tetrahydrofuran, dioxan or also mixtures.

The reaction of activated derivatives of the carboxylic acids of the formula III with cephem compounds of the formula II is preferably carried out in an alkaline medium above pH 7. For this, a base is added to the reaction mixture, such as, preferably, potassium carbonate or sodium carbonate, potassium bicarbonate or sodium bicarbonate, potassium hydroxide or sodium hydroxide, pyridine or a trialkylamine, such as, for example, triethylamine, N-methylmorpholine, ethyldiisopropylamine or potassium tert.-butylate.

Cephem compounds of the formula I can also be obtained by splitting off the radical $R^1$, if it does not denote hydrogen, in compounds of the formula IV and/or converting the radical $X'$, if it does not denote X, into X.

Thus, the radical $R^1$ can be split off using the gentle methods which are generally customary in β-lactam chemistry and peptide chemistry, such as hydrolysis in acids; preferably formic acid or trifluoroacetic acid, or by hydrogenolysis in the presence of noble metal catalysts. However, depending on the protective group, special reagents for splitting off can also be employed, such as, for example, optionally substituted thioureas for removing α-halogenoacyl groups.

The conversion of the group $X'$, if it does not denote X, into X can also be brought about by means of the gentle hydrolytic or hydrogenolytic methods which are customary in β-lactam chemistry and peptide chemistry, and hydrolyses in inorganic and organic acids, such as, preferably, trifluoroacetic acid or dilute formic acid, should be mentioned in particular.

Esters, which are obtained in the reaction according to the invention, of the formulae I and IV in which A denotes a radical which can be easily split off can, if desired, be converted into compounds of the formula I or IV in which A denotes hydrogen or a physiologically acceptable cation, in a gentle manner which is known from the literature, for example hydrolytically or hydrogenolytically, as has been described above.

In an analogous manner, it is also possible to split off the $R^3$ group from the radical $X'$ when this denotes $-CH_2CO_2R^3$.

Lactams of the formula II in which n=0 can preferably be oxidized as free acids or as esters, but also as salts.

It is advantageous first to protect the 7-amino group by amino-protective groups which can be easily split off, such as are customary, for example, in peptide chemistry. Examples of groups which can be split off under acid conditions and which can be employed are: tert.-butyl, benzhydryl, tert.-butoxycarbonyl, trityl, benzyloxycarbonyl, 3,5-dimethoxybenzyloxycarbonyl or trimethylsilyl. It has also proved suitable to protect the amino group in the form of a Schiff's base, which can be split under acid conditions, by reaction with reactive carbonyl compounds, such as, for example, benzaldehyde, salicylaldehyde, p-nitrobenzaldehyde, furfurol, 5-nitrofurfurol, acetylacetone or ethyl acetoacetate. The Schiff's base can also be split by reaction with hydrazine or phenylhydrazine, preferably with Girard reagent or 2,4-dinitrophenylhydrazine.

Suitable methods for the oxidation of the cephem compound II in which n=0 are methods which are known from the literature and which lead to the formation of sulfoxides by the oxidation of sulfides (compare, for example, Methodicum Chimicum, volume 7 (1976), page 693-698).

Examples of oxidizing agents which have proved suitable are peroxides, hydroperoxides, peracids, hydrogen superoxide and mixtures thereof with inorganic and organic, oxidation-resistant acids, such as, for example, phosphoric acid, formic acid, acetic acid and trifluoroacetic acid. The peracids can also be produced in situ by mixing with hydrogen peroxide. 3-Chloroperbenzoic acid has proved particularly suitable. It is advantageously employed direct.

Suitable solvents for the oxidation are all the solvents which are stable under the reaction conditions, such as, for example, dioxan, tetrahydrofuran, chloroform, methylene chloride, acetic acid, formic acid, trifluoroacetic acid, benzene, tetramethylurea, dimethylformamide or dimethylacetamide.

The amount of oxidizing agent is at least 2 oxidation equivalents (corresponding to one active oxygen atom). However, it is also possible to introduce a slight excess into the reaction.

The reaction temperature is in the range between about $-20°$ and $+80°$ C., but preferably between $-20°$ and room temperature.

The cephem compounds II in which n=1, which are oxidized on the sulfur to the sulfoxide, can exist in the R configuration or S configuration. (For characterization of the configuration, compare Angew. Chemie 78 (1966), page 413).

Cephem compounds of the formula II in which n=0 preferentially give the R-sulfoxides when the amino group is protected in the form of a Schiff's base.

Acylamino-protective groups on the 7-amino group predominantly give the 1-sulfoxides with the S configuration. The two configuration isomers can be differentiated and separated by chromatography. NMR spectroscopy can also be used for differentiation between the R-sulfoxides and S-sulfoxides (compare E. H. Flynn, Cephalosporins and Penicillins, Chemistry and Biology, Academic Press, New York and London, 1972).

Compounds of the formula I and IV in which n is 1 can also be obtained by interchanging the stages, described above, of oxidation of cephem compounds II to the sulfoxide and the subsequent acylation with a carboxylic acid III or an activated derivative thereof.

Thus, the cephem compounds II in which n is 0 and A has the abovementioned meanings can first be reacted with a carboxylic acid III, in which $R^1$, $X'$ and Y have the abovementioned meanings, or an activated derivative thereof, to give a compound of the formula IV in which $R^1$, $X'$, Y and A have the abovementioned meanings and n is 0. The subsequent oxidation to the sulfoxide can be carried out under the reaction conditions described for the oxidation of the lactams of the formula II in which n=0 to lactams of the formula II in which n=1. Protection of the 7-amino group is, of course, superfluous, since, because of the preceding acylation with the carboxylic acids of the formula III, the 7-amino group is no longer attacked by the oxidizing agent. Oxidation of the compounds I and IV gives predominantly sulfoxides with the S configuration, with which small amounts of sulfoxides with the R configuration, which can be separated off in the manner described above, can also be mixed.

The carboxylic acids III used for the acylation can be manufactured by various processes. Thus, for example, compounds of the formula III in which Y denotes halogen are obtained, for example, by reacting compounds of the formula V

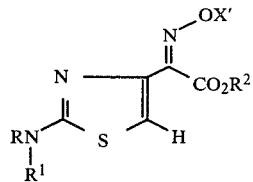

in which $R^1$ and $X'$ have the abovementioned meanings and $R^2$ denotes an alkyl radical with 1–4 C atoms or an aralkyl radical, such as, preferably, benzyl or phenylethyl, with a halogenating reagent, and optionally converting the radical $R^1$ and/or the radical $X'$ into the most favorable form for the subsequent reactions, and/or converting the ester V thus obtained into the carboxylic acid having the general formula III, in a manner which is in itself known.

Suitable halogenating agents which can be employed are the elementary halogens, such as, preferably, bromine and chlorine, trihalogeno-isocyanuric acids, such as, preferably, trichloroisocyanuric acid, N-halogenoamides, such as, preferably, chloramine-T, N-chloroacetamide and N-bromoacetamide, N-halogenoimides, such as, preferably, N-chlorosuccinimide, N-bromosuccinimide, N-chloro-phthalimide and N-bromophthalimide, or alkyl hypochlorites, such as, for example, tert.-butyl hypochlorite. The reaction is as a rule carried out in a solvent which does not adversely affect the reaction, or even enables the reaction to proceed in the desired direction. Thus, a polar solvent containing hydroxyl groups which promotes the formation of positive halogen ions, that is to say, preferably, formic acid, glacial acetic acid, water and alkanols such as, for example, methanol, ethanol or isopropanol, is advisable in the case of alkyl hypochlorites, N-halogenoamides and N-halogenoimides. In addition, but above all when an elementary halogen is used, solvents such as chloroform, methylene chloride, tetrahydrofuran, dioxan or dimethylformamide or mixtures thereof with one another or with the abovementioned solvents containing hydroxyl groups can also be recommended.

The reaction temperature is not critical, but is preferably in the range between about $-20°$ and room temperature.

Compounds of the formula III in which Y denotes halogen can furthermore be prepared by reacting thiourea with oximes of the formula

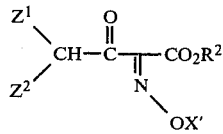

in which $Z^1$ and $Z^2$ can be identical or different and represent bromine, chlorine or fluorine and $X'$ as well as $R^2$ have the abovementioned meanings, by appropriately subsequently introducing $R^1$, in the meaning of an amino-protective group which, as defined above, is known from peptide chemistry, and/or by saponifying the ester of the formula V thus obtained to give the carboxylic acid of the general formula III.

The reaction is appropriately carried out with a stoichiometric amount of thiourea in a water-containing solvent, such as, for example, ethanol or acetone. The reaction should be carried out at room temperature and should last a maximum of about 2 to 3 hours.

Compounds of the formula III in which Y denotes methyl can be prepared, for example, by reacting thiourea with compounds of the formula

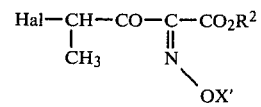

in which Hal denotes chlorine or bromine and $X'$ as well as $R^2$ have the abovementioned meanings, by appropriately subsequently introducing $R^1$, in the meaning of an amino-protective group which, as defined above, is known from peptide chemistry, and/or by saponifying the ester to give the carboxylic acids of the formula III.

The reaction is appropriately carried out with a stoichiometric amount of thiourea in a water-containing solvent, such as acetone or ethanol, at room temperature for a maximum of about 2 to 3 hours.

The starting compounds of the formula V are known from the literature or can be manufactured by processes which are known from the literature.

If in the general formulae III and IV the radical $R^1$ represents a group which can be easily removed and is known from peptide chemistry as an amino-protective group, it can be introduced into the amino group in the manner known, from peptide chemistry, for amino-protective groups. For example, if $R^1$ represents the trityl group, it can be introduced using triphenylchloromethane, the reaction appropriately being carried out in an organic solvent, such as, for example, halogenated hydrocarbons, in the presence of bases, such as, preferably, triethylamine.

If in the formulae III and V $X'$ represents a group which can be easily split off, it can be introduced in a manner which is customarily used, by the expert, for the protection of hydroxyl groups.

It is appropriate, not only in the preparation of the starting materials III and V, which contain a group

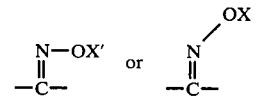

in the synposition, but also in the preparation of all intermediate compounds and in their further reaction to give IV and I, to apply reaction conditions which are as mild as possible, such as are known, to the expert, from the literature for reactions with syn compounds, such as, for example, no elevated temperature, no prolonged reaction times, no substantial excesses of acid reactants and the like, in order to avoid any possible flipping-over of the oxime group into the anti form.

The compounds of the formula I obtained according to the invention exhibit remarkably good antibacterial activities against both Gram positive and Gram negative bacterial germs.

The new compounds also have an unexpectedly good action against penicillinase-forming and cephalosporinase-forming bacteria. Since they additionally exhibit favorable toxicological and pharmacological properties, they are valuable chemotherapeutic agents.

The invention thus also relates to medicinal formulations for the treatment of microbial infections, which contain one or more of the compounds according to the invention.

The products according to the invention can also be used in combination with other active compounds, for example from the penicillin, cephalosporin or aminoglycoside series.

The compounds of the formula I can be administered orally, intramuscularly or intravenously.

Medicinal formulations which contain one or more compounds of the general formula I as the active compound can be manufactured by mixing the compounds of the general formula I with one or more pharmacologically acceptable excipients or diluents, such as, for example, fillers, emulsifiers, lubricants, flavor-improving agents, dyestuffs or buffer substances, and bringing the mixture into a suitable galenical formulation form, such as, for example, tablets, dragees, capsules or a solution or suspension suitable for parenteral administration. Examples of excipients or diluents which may be mentioned are tragacanth, lactose, talc, agar-agar, polyglycols, ethanol and water. Suspensions or solutions in water are preferably used for parenteral administration. It is also possible to administer the active compounds as such, without excipients or diluents, in a suitable form, for example in capsules.

Suitable doses of the compounds of the general formula I are about 0.5 to 20 g/day, preferably 0.5 to 4 g/day, for an adult having a body weight of about 60 kg. Individual doses or, in general, multiple doses, can be administered, it being possible for the individual dose to contain the active compound in an amount of about 50 to 1,000 mg, preferably 100 to 500 mg.

In addition to the compounds mentioned in the embodiment examples, the following compounds, for example, can be manufactured according to the invention: the 1-S-oxide of 7-[α-syn-methoximino-α-(2-amino-5-methyl-thiazol-4-yl)-acetamido]-cephalosporanic acid, the 1-S-oxide of 7-[α-syn-methoximino-α-(2-amino-5-bromo-thiazol-4-yl)-acetamido]-cephalosporanic acid, 7-[α-syn-ethoximino-α-(2-amino-5-methyl-thiazol-4-yl)-acetamido]-cephalosporanic acid, and its 1-S-oxide, 7-[α-syn-ethoximino-α-(2-amino-5-bromothiazol-4-yl)-acetamido]-cephalosporanic acid, and its 1-S-oxide, 7-[α-syn-n-propoximino-α-(2-amino-5-methyl-thiazol-4-yl)-acetamido]-cephalosporanic acid, and its 1-S-oxide, 7-[α-syn-n-propoximino-α-(2-amino-5-bromo-thiazol-4-yl)-acetamido]-cephalosporanic acid, and its 1-S-oxide, 7-[α-syn-n-propoximino-α-(2-amino-5-chloro-thiazol-4-yl)-acetamido]-cephalosporanic acid, and its 1-S-oxide, 7-[α-syn-isopropoximino-α-(2-amino-5-methyl-thiazol-4-yl)-acetamido]-cephalosporanic acid, and its 1-S-oxide, 7-[α-syn-isopropoximino-α-(2-amino-5-bromo-thiazol-4-yl)-acetamido]-cephalosporanic acid, and its 1-S-oxide, 7-[α-syn-iso-propoximino-α-(2-amino-5-chloro-thiazol-4-yl)-acetamido]-cephalosporanic acid, and its 1-S-oxide, 7-[α-syn-n-butoximino-α-(2-amino-5-methyl-thiazol-4-yl)-acetamido]-cephalosporanic acid, and its 1-S-oxide, 7-[α-syn-n-butoximino-α-(2-amino-5-chloro-thiazol-4-yl)-acetamido]-cephalosporanic acid, and its 1-S-oxide, 7-[α-syn-carboxymethoximino-α-(2-amino-5-methyl-thiazol-4-yl)-acetamido]-cephalosporanic acid, and its 1-S-oxide, 7-[α-syn-carboxymethoximino-α-(2-amino-5-bromo-thiazol-4-yl)-acetamido]-cephalosporanic acid, and its 1-S-oxide, 7-[α-syn-ethoxy-carbonyl-methoximino-α-(2-amino-5-methyl-thiazol-4-yl)-acetamido]-cephalosporanic acid, and its 1-S-oxide, 7-[α-syn-ethoxycarbonyl-methoximino-α-(2-amino-5-bromo-thiazol-4-yl)-acetamido]-cephalosporanic acid, and its 1-S-oxide, 7-[α-syn-ethoxycarbonyl-methoximino-α-(2-amino-5-chloro-thiazol-4-yl)-acetamido]-cephalosporanic acid, and its 1-S-oxide, 7-[α-syn-carboxymethoximino-α-(2-amino-5-chloro-thiazol-4-yl)-acetamido]-cephalosporanic acid, and its 1-S-oxide, 7-[α-syn-cyanomethoximino-α-(2-amino-5-methyl-thiazol-4-yl)-acetamido]-cephalosporanic acid, and its 1-S-oxide, 7-[α-syn-cyanomethoximino-α-(2-amino-5-bromothiazol-4-yl)-acetamido]-cephalosporanic acid, and its 1-S-oxide, 7-[α-syn-cyanomethoximino-α-(2-amino-5-chloro-thiazol-4-yl)-acetamido]-cephalosporanic acid, and its 1-S-oxide, 7-[α-syn-aminocarbonylmethoximino-α-(2-amino-5-methyl-thiazol-4-yl)-acetamido]-cephalosporanic acid, and its 1-S-oxide, 7-[α-syn-aminocarbonyl-methoximino-α-(2-amino-5-bromo-thiazol-4-yl)-acetamido]-cephalosporanic acid, and its 1-S-oxide, 7-[α-syn-aminocarbonyl-methoximino-α-(2-amino-5-chloro-thiazol-4-yl)-acetamido]-cephalosporanic acid, and its 1-S-oxide, 7-[α-syn-hydroximino-α-(2-amino-5-methyl-thiazol-4-yl)-acetamido]-cephalosporanic acid, and its 1-S-oxide, 7-[α-syn-hydroximino-α-(2-amino-5-bromo-thiazol-4-yl)-acetamido]-cephalosporanic acid, and its 1-S-oxide, 7-[α-syn-hydroximino-α-(2-amino-5-chloro-thiazol-4-yl)-acetamido]-cephalosporanic acid, and its 1-S-oxide, 7-[α-syn-hydroximino-α-(2-amino-5-fluoro-thiazol-4-yl)-acetamido]-cephalosporanic acid, and its 1-S-oxide, 7-[α-syn-methoximino-α-(2-amino-5-fluoro-thiazol-4-yl)-acetamido]-cephalosporanic acid, and its 1-S-oxide, 7-[α-syn-ethoximino-α-(2-amino-5-fluoro-thiazol-4-yl)-acetamido]-cephalosporanic acid, and its 1-S-oxide, 7-[α-syn-n-propoximino-α-(2-amino-5-fluoro-thiazol-4-yl)-acetamido]-cephalosporanic acid, and its 1-S-oxide, 7-[α-syn-iso-propoximino-α-(2-amino-5-fluoro-thiazol-4-yl)-acetamido]-cephalosporanic acid, and its 1-S-oxide, 7-[α-syn-n-butoximino-α-(2-amino-5-fluoro-thiazol-4-yl)-acetamido]-cephalosporanic acid, and its 1-S-oxide, 7-[α-syn-carboxymethoximino-α-(2-amino-5-fluoro-thiazol-4-yl)-acetamido]-cephalosporanic acid, and its 1-S-oxide, 7-[α-syn-ethoxycarbonylmethoximino-α-(2-amino-5-fluoro-thiazol-4-yl)-acetamido]-cephalosporanic acid, and its 1-S-oxide, 7-[α-syn-cyanomethoximino-α-(2-amino-5-fluoro-thiazol-4-yl)-acetamido]-cephalosporanic acid, and its 1-S-oxide and 7-[α-syn-aminocarbonylmethoximino-α-(2-amino-5-fluoro-thiazol-4-yl)-acetamido]-cephalosporanic acid, and its 1-S-oxide.

The Examples illustrate the invention, but without limiting it.

The $R_F$ values indicated in the Examples were determined by thin layer chromatography on silica gel finished plates 60 F 254 from Messrs. Merck, Darmstadt.

EXAMPLE 1

7-[α-syn-Methoximino-α-(2-amino-5-methyl-thiazol-4-yl)-acetamido]-cephalosporanic acid Stage 1

A solution of 22.8 g (0.3 mole) of sodium nitrite in 45 ml of $H_2O$ was slowly added to 43 g (0.3 mole) of ethyl propionylacetate in 45 ml of glacial acetic acid at 20°–25°, whilst stirring and cooling. The mixture was stirred at 10° for 1 hour, 90 ml of water were added and the mixture was stirred at room temperature for 1 hour and extracted four times with 75 ml of ether each time. The combined ether extracts were shaken with NaHCO$_3$ solution until neutral, dried over sodium sulphate and evaporated to dryness.

55 g of ethyl α-hydroximino-propionylacetate were thus obtained as a yellow oil which crystallizes at low temperature; n$_D^{20}$ of the oil: 1.4413, R$_F$: 0.3 (CHCl$_3$/acetone=20/1). The oil was employed without further purification.

Stage 2

The oil obtained in Stage 1 was dissolved in 250 ml of acetone, 60 g of K$_2$CO$_3$ were added and 38.5 g (0.3 mole) of dimethyl sulfate were added in the course of 30 minutes. After stirring the mixture at room temperature for two hours, it was poured onto 200 g of ice, stirred with 500 ml of H$_2$O and extracted once with 150 ml of ether and three times with CH$_2$Cl$_2$. After drying over Na$_2$SO$_4$, the combined organic extracts were freed from solvent and gave 45 g of ethyl α-methoximino-propionylacetate as an oil.

R$_F$: 0.63 (CHCl$_3$/acetone=20/1)

NMR (DMSO-d$_6$): δ=0.9–1.4 ppm (2×tr., 6H, OCH$_2$C$\underline{H}_3$ and COCH$_2$C$\underline{H}_3$), δ=2.85 ppm (q, 2H, COC$\underline{H}_2$CH$_3$), δ=4.05 ppm and δ=4.10 ppm (2×s, 1:4; 3H, OCH$_3$) and δ=4.30 ppm (q, 2H, OC$\underline{H}_2$CH$_3$).

The product was employed without further purification.

Stage 3

45 g of the oil obtained in Stage 2 were dissolved in 300 ml of CH$_2$Cl$_2$, the solution was cooled to 20° and a solution of 39 g (0.24 mole) of Br$_2$ in 50 ml of CH$_2$Cl$_2$ was added dropwise. The mixture was then stirred at room temperature for a further 1½ hours, extracted by shaking twice with 300 ml of H$_2$O each time, dried over Na$_2$SO$_4$ and freed from solvent in vacuo. 60 g of ethyl α-methoximino-γ-bromo-propionyl-acetate were thus obtained as a light brown oil.

R$_F$=0.38 (CHCl$_3$)

The product was employed without further purification.

Stage 4

13.3 g of the oil obtained in Stage 3, dissolved in 13 ml of ethanol, were added to a solution of 3.8 g (0.5 mole) of thiourea in 13 ml of ethanol and 27 ml of H$_2$O at 16°–18°. After adding a further 13 ml of ethanol, the mixture was stirred at room temperature for 1 hour. The pH was adjusted to 5 with saturated KHCO$_3$ solution, whilst monitoring the pH. 4.6 g (56%) of ethyl α-syn-methoximino-α-(2-amino-5-methyl-thiazol-4-yl)-acetate were obtained by filtration.

Melting point: 135°–136°

NMR (DMSO-d$_6$) δ=1.2 ppm (t, 3H, OCH$_2$—C$\underline{H}_3$), δ=4.25 ppm (q, 2H, OC$\underline{H}_2$—CH$_3$), δ=142 Hz (s, 3H, CH$_3$, syn) and δ=232 Hz (s, 3H, OCH$_3$, syn).

Stage 5

12.2 g (0.05 mole) of the ester obtained in Stage 4 were dissolved in 23.7 ml of dimethylformamide, 47.5 ml of CH$_2$Cl$_2$ were added and the mixture was cooled to −10°. After adding 7.35 ml of triethylamine, the mixture was cooled to −35° and a total of 16.5 g of trityl chloride was added in portions, whilst stirring. The solution was stirred for 2½ hours, without cooling, diluted with 100 ml of CH$_2$Cl$_2$ and washed successively with twice 50 ml of 1 N HCl and three times 100 ml of H$_2$O. The organic phase was dried over Na$_2$SO$_4$ and freed from solvent in vacuo.

The oil thus obtained was employed without further purification.

Stage 6

The oil obtained in Stage 5 was dissolved in 240 ml of ethanol, and 10 ml of 10 N NaOH were added. After stirring the mixture at room temperature for five hours, the product was filtered off.

10.3 g of the sodium salt of α-syn-methoximino-α-(2-tritylamino-5-methyl-thiazol-4-yl)-acetic acid were thus obtained, and the product was employed without further purification.

Stage 7

23 ml of 2 N HCl were added to 9.6 g (20 mmoles) of the sodium salt obtained in Stage 6, in 80 ml of CH$_2$Cl$_2$ and 10 ml of ether, whilst cooling with ice. The CH$_2$Cl$_2$ was separated off and the aqueous phase was again extracted with 10 ml of CH$_2$Cl$_2$. After drying the combined CH$_2$Cl$_2$ phases over Na$_2$SO$_4$ and removing the solvent in vacuo, a foam remained: α-syn-methoximino-α-(2-tritylamino-5-methylthiazol-4-yl)-acetic acid, which was employed without further purification.

Stage 8

The product obtained in Stage 7 was dissolved in 30 ml of CH$_2$Cl$_2$, the solution was cooled under N$_2$ in an ice bath and 2.35 g of dicyclohexylcarbodiimide were added. The mixture was stirred at 0° for ½ hour and at room temperature for 1 hour, the dicyclohexylurea formed was filtered off, the filtrate was cooled to −20° and a solution of 2.72 g of 7-aminocephalosporanic acid and 3.3 ml of triethylamine in 40 ml of CH$_2$Cl$_2$ was added. The mixture was stirred at room temperature for 2½ hours and then adjusted to pH 2.75 with 1 N HCl.

The CH$_2$Cl$_2$ phase was washed twice with 70 ml of H$_2$O, dried over Na$_2$SO$_4$ and evaporated to dryness in vacuo.

The residue was taken up in a mixture of 50 ml of dioxan and 50 ml of ether, 2.1 ml (20 mmoles) of diethylamine were added and ether was added until turbidity started to appear. After 48 hours at −5°, 2.6 g of the diethylammonium salt of α-syn-methoximino-α-(2-tritylamino-5-methyl-thiazol-4-yl)-acetic acid could be collected by filtration.

7.0 g of a mixture of the diethylammonium salts of α-syn-methoximino-(2-tritylamino-5-methyl-thiazol-4-yl)-acetic acid and 7-[α-syn-methoximino-α-(2-tritylamino-5-methyl-thiazol-4-yl)-acetamido]-cephalosporanic acid could be obtained by evaporating the mother liquor.

Stage 9

7.0 g of the diethylammonium salt mixture obtained in Stage 8 were dissolved in a mixture of 30 ml of 98% strength formic acid and 20 ml of H$_2$O and the solution was stirred at room temperature for 2½ hours. The triphenylcarbinol formed was filtered off, the filtrate was diluted to 250 ml with H$_2$O and filtered again and the filtrate was concentrated to about 30 ml on a rotary evaporator.

The product phase was adjusted to pH 8.0 with saturated NaHCO$_3$ solution, extracted with ethyl acetate, covered with a layer of 50 ml of ethyl acetate and brought to pH 2.0 with 2 N HCl. The aqueous solution was extracted five times with ethyl acetate and the combined ethyl acetate extracts were dried over Na$_2$SO$_4$ and concentrated on a rotary evaporator. 20 ml of ether were added to the oil formed and the mixture was stirred for 1 hour, whereupon it solidified. The precipitate was filtered off.

1.5 g of 7-[α-syn-methoximino-α-(2-aminothiazol-4-yl)-acetamido]-cephalosporanic acid with the R$_F$ value 0.53 (ethyl acetate:iso-propanol:water = 6:4:3) were thus obtained.

Melting point: 125°–135° (decomposition)

NMR (DMSO-d$_6$): δ=2.0 ppm (s, 3H, OCOC$\underline{H}_3$), δ=2.3 ppm (s, 3H, thiazole-C$\underline{H}_3$), δ=3.8 ppm [231 Hz] (s, 3H, N—OCH$_3$, syn), δ=4.7 ppm (AB, 2H, 3'-CH$_2$), δ=5.1 ppm (d, 1H, 6-H) and δ=5.6 ppm (q, 1H, 7-H).

EXAMPLE 2

7-[α-syn-Methoximino-α-(2-amino-5-bromo-thiazol-4-yl)-acetamido]-cephalosporanic acid

Stage 1

6.39 g of bromine in 20 ml of glacial acetic acid were added dropwise, at 15°, to 9.15 g (40 mmoles) of ethyl α-syn-methoximino-α-(2-amino-thiazol-4-yl)-acetate, dissolved in 50 ml of glacial acetic acid. When the addition had ended, the mixture was subsequently stirred for a further 15 minutes and added to 150 g of ice. The precipitate was filtered off and washed with water:

10.9 g of ethyl α-syn-methoximino-α-(2-amino-5-bromo-thiazol-4-yl)-acetate with a melting point of 149°–151° could thus be obtained. Recrystallisation from ethanol:

Melting point: 157°–158°

NMR (DMSO-d$_6$): δ=1.27 ppm (t, 3H, OCH$_2$C$\underline{H}_3$), δ=3.93 ppm [236 Hz] (s, 3H, NOC$\underline{H}_3$), δ=4.3 ppm (q, 2H, OC$\underline{H}_2$CH$_3$) and δ=7.4 ppm (s broad, 2H, NH$_2$).

Stage 2

3 g of the ester obtained in Stage 1 were dissolved in 8 ml of methanol, and 20 ml of 80% strength hydrazine hydrate were added at 50° C. The mixture was stirred at room temperature for 4 hours and cooled to 0° C. and the precipitate was filtered off.

2.5 g of α-syn-methoximino-α-(2-amino-5-bromo-thiazol-4-yl)-acetohydrazide with a melting point of 200° (decomposition) were thus obtained.

The crystals were further processed immediately, since they decomposed very rapidly.

Stage 3

1.5 g of the hydrazide prepared in Stage 2 were dissolved in 25 ml of dimethylformamide, the solution was cooled to −20° C., 3.3 ml of a 4.51 N solution of HCl in dioxan were added and 0.6 ml of tert.-butyl nitrite in 4 ml of dioxan were then slowly added.

The light yellow solution was stirred at −20° for ½ hour and 1.5 g of triethylamine in 10 ml of dioxan were added. A solution of 1.36 g of 7-aminocephalosporanic acid in 10 ml of dimethylformamide and 1.0 g of triethylamine was then added dropwise. A further 0.5 g of triethylamine in 6 ml of dioxan was then added in 3 portions within the following hour. The product phase was added to 100 ml of H$_2$O, extracted three times with ethyl acetate and adjusted to pH 4.0, the insoluble material was filtered off and the filtrate was further acidified to pH 1.5 with 2 N HCl.

The mixture was extracted five times with ethyl acetate and, after drying over Na$_2$SO$_4$, the combined ethyl acetate extracts were concentrated. An oil was formed, which solidified after trituration with ether. 650 mg of 7-[α-syn-methoximino-α-(2-amino-5-bromo-thiazol-4-yl)-acetamido]-cephalosporanic acid could thus be obtained.

Melting point: 135°–145° (decomposition)

IR (KBr): 1,770 cm$^{-1}$ (β-lactam) and 1,720 cm$^{-1}$ (acetate).

NMR (DMSO-d$_6$): δ=2.0 ppm (s, 3H, OCOC$\underline{H}_3$), δ=3.9 ppm [232 Hz] (s, 3H, NOC$\underline{H}_3$) and δ=9.5 ppm (d, 1H, —N$\underline{H}$—CO—).

EXAMPLE 3

7-[α-syn-n-Butoximino-α-(2-amino-5-bromo-thiazol-4-yl)-acetamido]-cephalosporanic acid

Stage 1

In a manner analogous to that described in Example 2, Stage 1, 11 g of ethyl α-syn-n-butoximino-α-(2-amino-thiazol-4-yl)-acetic acid with 6.4 g of bromine gave 11.7 g of ethyl α-syn-n-butoximino-α-(2-amino-5-bromo-thiazol-4-yl)-acetate with a melting point of 130°–140° (ethanol).

NMR (DMSO-d$_6$): δ=0.7–1.9 ppm (m, 10H, —C$\underline{H}_2$—C$\underline{H}_2$—C$\underline{H}_3$ and —OCH$_2$C$\underline{H}_3$), δ=4.15 ppm [248 Hz] (t, 2H, —OC$\underline{H}_2$—CH$_2$—) and δ=4.3 ppm (q, 2H, —O—C$\underline{H}_2$—CH$_3$).

Stage 2

In a manner analogous to that described in Example 2, Stage 2, 3.2 g of the ester obtained in Stage 1 gave 2.8 g of α-syn-n-butoximino-α-(2-amino-5-bromo-thiazol-4-yl)-acetohydrazide.

Melting point = ~190° (decomposition)

Because of its instability, the product was further processed immediately.

Stage 3

In a manner analogous to that described in Example 2, Stage 3, 1.68 g of the hydrazide obtained in Stage 2 gave 520 mg of 7-[α-syn-n-butoximino-α-(2-amino-5-bromo-thiazol-4-yl)-acetamido]-cephalosporanic acid.

Melting point: 140°–150° (decomposition)

IR (KBr): 1,770 cm$^{-1}$ (β-lactam) and 1,725 cm$^{-1}$ (OCOCH$_3$).

NMR (DMSO-d$_6$) δ=0.7–1.9 ppm (m, 7H, C$\underline{H}_2$—C$\underline{H}_2$—C$\underline{H}_3$), δ=2.07 ppm (s, 3H, OCOCH$_3$), δ=4.15 ppm [244 Hz] (t, 2H, —O—C$\underline{H}_2$—CH$_2$) and δ=9.4 ppm (d, 1H, N$\underline{H}$CO).

EXAMPLE 4

7-[α-syn-Methoximino-α-(2-amino-5-chloro-thiazol-4-yl)-acetamido]-cephalosporanic acid

Stage 1

50 g of α-syn-methoximino-α-(2-amino-thiazol-4-yl)-acetic acid were suspended in a mixture of 300 ml of CHCl$_3$ and 150 ml of glacial acetic acid, and 17.5 g of Cl$_2$ in 200 ml of glacial acetic acid were added at 0°–10°, whilst stirring. The mixture was stirred at 0° for ½ hour and the precipitate was filtered off. The precipitate was once more suspended in CHCl$_3$ and again filtered off.

The filtration residue was refluxed in 190 ml of tetrahydrofuran for 15 minutes and the mixture was stirred at room temperature for 2 hours. 30.3 g of α-synmethoximino-α-(2-amino-5-chloro-thiazol-4-yl)-acetic acid×1 HCl×1H$_2$O×1 tetrahydrofuran.

Melting point: 150°–153°.

Stage 2

29 g of the acid obtained in Stage 1 were dissolved in 100 ml of methanol, and 4.85 g of sodium methylate were added. After stirring at room temperature for fifteen minutes, the mixture was evaporated to dryness to vacuo and the residue was extracted at the boil three times with 75 ml of dry tetrahydrofuran each time. The filtered tetrahydrofuran mother liquors were evaporated and the residue was recrystallised from a very little methanol. 13.5 g of α-syn-methoximino-α-(2-amino-5-chloro-thiazol-4-yl)-acetic acid×1 methanol were thus obtained.

Melting point: 129°–130° (decomposition)

NMR (DMSO-d$_6$): δ=3.1 ppm (s, 3H, CH$_3$OH) and δ=3.9 ppm [234 Hz] (s, 3H, N—OC$\underline{H}_3$)

Stage 3

8.0 g of the carboxylic acid obtained in Stage 2 were dissolved in 100 ml of dimethylacetamide, 100 ml of carbon tetrachloride were added and the mixture was freed from carbon tetrachloride on a rotary evaporator, in order to remove the methanol contained in Stage 2. The residue was then cooled to −20° and 3.4 g of chloroacetyl chloride, dissolved in 10 ml of dimethylacetamide, were added. The temperature was kept at −20° C. for ¼ hour, at 0° C. for ½ hour and then at +10° for ¼ hour.

The mixture was added to ice and extracted three times with ethyl acetate. After drying over Na$_2$SO$_4$ and evaporating off the solvent, 8.2 g of α-syn-methoximino-α-(2-chloroacetylamino-5-chloro-thiazol-4-yl)-acetic acid remained as a pale yellow oil. R$_F$: 0.54 (ethyl acetate: iso-propanol: H$_2$O=6:4:3).

NMR (DMSO-d$_6$) δ=3.9 ppm [232 Hz] (s, 3H, NOC$\underline{H}_3$) and δ=4.4 ppm (s, 2H, COC$\underline{H}_2$Cl)

Stage 4

3.1 g of the carboxylic acid prepared in Stage 3 were dissolved in 15 ml of CH$_2$Cl$_2$, and 1.45 ml of triethylamine were added. The mixture was cooled to 0° and 0.5 ml of thionyl chloride, dissolved in 5 ml of methylene chloride, was added dropwise.

The mixture was stirred at 0° for ¼ hour and, after adding a further 1.3 ml of triethylamine, a solution of 2.5 g of 7-aminocephalosporanic acid in 20 ml of methylene chloride and 2.8 ml of triethylamine was added. The mixture was subsequently stirred for 1 hour and freed from solvent in vacuo and the residue was taken up in 40 ml of H$_2$O. The pH was adjusted to 7.0, the solution was extracted twice with 20 ml of ethyl acetate and adjusted to pH 4.0 and the reaction mixture was freed from the 7-aminocephalosporanic acid which had precipitated out and acidified further to pH 2.0. 1.5 g of 7-[α-syn-methoximino-α-(2-chloroacetylamino-5-chloro-thiazol-4-yl)-acetamido]-cephalosporanic acid could be collected by filtration.

R$_F$: 0.49 (ethyl acetate: iso-propanol: H$_2$O=6:4:3)

NMR (DMSO-d$_6$): δ=2.05 ppm (s, 3H, OCOC$\underline{H}_3$), δ=3.9 ppm [234 Hz] (s, 3H, NOC$\underline{H}_3$), δ=4.4 ppm (s, 2H, COC$\underline{H}_2$Cl) and δ=9.7 ppm (d, 1H, —N$\underline{H}$—CO—)

Stage 5

400 mg of thiourea were added to 2.9 g of the product prepared in Stage 4, in 50 ml of a 1:1 mixture of ethanol and tetrahydrofuran, and the mixture was stirred at room temperature for 15 hours. It was concentrated to dryness in vacuo and the residue was taken up in 20 ml of water.

The solid was filtered off and again stirred up in 10 ml of a 1:1 water/ethanol mixture and filtered off.

0.92 g of 7-[α-syn-methoximino-α-(2-amino-5-chloro-thiazol-4-yl)-acetamido]-cephalosporanic acid was thus obtained.

Melting point=135°–145° (decomposition)

IR (KBr): 1,770 cm$^{-1}$ (β-lactam) and 1,720 cm$^{-1}$ (acetate band)

NMR (DMSO-d$_6$): δ=2.0 ppm (s, 3H, OCOC$\underline{H}_3$), δ=3.85 ppm [231 Hz] (s, 3H, =NOCH$_3$) and δ=9.5 ppm (d, 1H, N$\underline{H}$CO)

EXAMPLE 5

7-[α-syn-Ethoximino-α-(2-amino-5-chloro-thiazol-4-yl)-acetamido]-cephalosporanic acid

Stage 1

In a manner analogous to that described in Example 4, Stage 1, 54 g of α-syn-ethoximino-α-(2-amino-thiazol-4-yl)-acetic acid gave 32.1 g of α-syn-ethoximino-α-(2-amino-5-chloro-thiazol-4-yl)-acetic acid×1 HCl×1 tetrahydrofuran: melting point: 106°–108° (decomposition)

Stage 2

In a manner analogous to that described in Example 4, Stage 2, 30.7 g of the acid obtained in Stage 1 gave 18.4 g of α-syn-ethoximino-α-(2-amino-5-chloro-thiazol-4-yl)-acetic acid×1 methanol.

NMR (DMSO-d$_6$): δ=3.15 ppm (s, 3H, CH$_3$OH), δ=1.2 ppm (t, 3H, OCH$_2$C$\underline{H}_3$) and δ=4.15 ppm [250 Hz] (q, 2H, OC$\underline{H}_2$CH$_3$)

Stage 3

In a manner analogous to that described in Example 4, Stage 3, 8.4 g of the carboxylic acid described in Stage 2 gave 7.4 g of α-syn-ethoximino-α-(2-chloroacetyl-amino-5-chloro-thiazol-4-yl)-acetic acid as a pale yellow oil.

R$_F$: 0.56 (ethyl acetate: iso-propanol: H$_2$O=6:4:3).

NMR(DMSO-d$_6$): δ=1.25 ppm (t, 3H, OCH$_2$C$\underline{H}_3$), δ=4.15 ppm [248 Hz] (q, 2H, OC$\underline{H}_2$CH$_3$) and δ=4.35 ppm (s, 2H, COC$\underline{H}_2$Cl)

Stage 4

In a manner analogous to that described in Example 4, Stage 4, 3.25 g of the carboxylic acid prepared in Stage 3 gave 1.9 g of 7-[α-syn-ethoximino-α-(2-chloroacetylamino-5-chloro-thiazol-4-yl)-acetamido]-cephalosporanic acid.

R$_F$=0.51 (ethyl acetate: iso-propanol: H$_2$O=6:4:3)

NMR (DMSO-d$_6$): δ=1.2 ppm (t, 3H, OCH$_2$C$\underline{H}_3$), δ=4.1 ppm [250 Hz] (q, 2H, OC$\underline{H}_2$CH$_3$), δ=2.05 ppm (s, 3H, OCOCH$_3$), δ=4.4 ppm (s, 2H, COC$\underline{H}_2$Cl) and δ=9.85 ppm (d, 1H, N$\underline{H}$CO)

Stage 5

In a manner analogous to that described in Example 4 Stage 5, 2.8 g of the product prepared in Stage 4 gave 860 mg of 7-[α-syn-ethoximino-α-(2-amino-5-chloro-thiazol-4-yl)-acetamido]-cephalosporanic acid.

Melting point: 140°–150° (decomposition)

IR (KBr): 1,775 cm$^{-1}$ (β-lactam) and 1,725 cm$^{-1}$ (acetate-O)

NMR (DMSO-d$_6$): δ=1.25 ppm (t, 3H, OCH$_2$CH$_3$), δ=2.0 ppm (s, 3H, OCOCH$_3$), δ=4.1 ppm [251 Hz] (q, 2H, OCH$_2$CH$_3$) and δ=9.7 ppm (d, 1H, NHCO)

EXAMPLE 6

The 1-S-oxide of 7-[α-syn-methoximino-α-(2-amino-5-chlorothiazol-4-yl)-acetaido]-cephalosporanic acid 980 mg of the product described in Example 4, Stage 5, were dissolved in 8 ml of 98% strength formic acid and 2 ml of methanol. The solution was cooled with ice, and 410 mg of 85% pure m-chloroperbenzoic acid, dissolved in 3 ml of tetrahydrofuran, were added, whilst cooling with ice. After stirring at room temperature for one hour, the solution was added dropwise to 100 ml of ether, the mixture was stirred for 1 hour and the solid was filtered off. The residue was again taken up in 10 ml of ether and the mixture was stirred for ¼ hour. 850 mg of the title compound could be obtained by filtration.

Melting point >300°

IR (KBr) 1,775 cm$^{-1}$ (β-lactam), 1,710 cm$^{-1}$ (OCOCH$_3$) and 1,030 cm$^{-1}$ (S→O)

NMR (DMSO-d$_6$): δ=2.0 ppm (s, 3H, OCOCH$_3$), δ=3.85 ppm [234 Hz] (s, 3H, NOCH$_3$) and δ=8.7 ppm (d, 1H, NHCO)

EXAMPLE 7

The 1-S-oxide of 7-[α-syn-ethoximino-α-(2-amino-5-chlorothiazol-4-yl)-acetamido]-cephalosporanic acid In a manner analogous to that indicated in Example 6, 1.06 g of the product prepared in Example 5, Stage 5, gave 910 mg of the title compound.

Melting point: 300°

IR (KBr): 1,770 cm$^{-1}$ (β-lactam), 1,710 cm$^{-1}$ (OCOCH$_3$) and 1,025 cm$^{-1}$ (S→O)

NMR (DMSO-d$_6$): δ=1.25 ppm (t, 3H, OCH$_2$CH$_3$), δ=2.05 ppm (s, 3H, OCOCH$_3$), δ=4.1 ppm [250 Hz] (q, 2H, OCH$_2$CH$_3$) and δ=8.65 ppm (d, 1H, CONH)

EXAMPLE 8

7-[α-syn-Hydroximino-α-(2-amino-5-chloro-thiazol-4-yl)-acetamido]-cephalosporanic acid

Stage 1

10 g of α-syn-trityloximino-α-(2-tritylaminothiazol-4-yl)-acetic acid are suspended in 200 ml of chloroform and the suspension is cooled to 0°. 15 ml of a 1 molar solution of Cl$_2$ in glacial acetic acid are added dropwise and the mixture is subsequently stirred for 2 hours. It is extracted with water a number of times, until the aqueous phase remains neutral. The organic phase is dried and concentrated to dryness in vacuo. 10.8 g of α-syn-trityloximino-α-(2-tritylamino-5-chlorothiazol-4-yl)-acetic acid are thus obtained.

NMR (DMSO-d$_6$) δ=8.3 ppm (broad s, NH) and δ=7.0–7.3 ppm (s, trityl-H).

Stage 2

3.5 g of the acid obtained in Stage 1 are suspended in 40 ml of toluene, and 315 mg of dimethylformamide are added, whereupon a clear solution is formed. 3.25 ml of a 2 molar solution of phosgene in toluene are added at −10° and the mixture is stirred at this temperature overnight. 1.36 g of 7-aminocephalosporanic acid, dissolved in 30 ml of CH$_2$Cl$_2$/2.0 g of triethylamine, are added to the suspension formed. The mixture is stirred at −10° for 1 hour and at room temperature for 2 hours. It is diluted with 20 ml of H$_2$O and the pH is adjusted to 2.0. The 7-aminocephalosporanic acid which has precipitated is filtered off and, after separating the phases, the organic layer is washed with H$_2$O. The solvent is removed in vacuo, the residue is taken up in acetone, 150 ml of diethylamine are added, the mixture is evaporated to dryness and the residue is stirred up with 20 ml of ether.

The resulting solid is stirred in 20 ml of 80% strength formic acid at 50° for 1 hour, the mixture is extracted twice with 20 ml of toluene and the product phase is evaporated. The residue is stirred in 20 ml of ethanol at room temperature for 3 hours, filtered off, taken up briefly in ethanol again, and again filtered off. After washing the residue with ether and drying in vacuo, 950 mg of 7-[α-syn-hydroximino-α-(2-amino-5-chlorothiazol-4-yl)-acetamido]-cephalosporanic acid remain.

NMR (DMSO-d$_6$): δ=9.4 ppm (d, 1H, NHCO), δ=7.2 ppm (s, broad, 2H, NH$_2$), δ=5.7 ppm (q, 1H, 7-H), δ=5.1 ppm (d, 1H, 6-H), δ=4.85 ppm (A B, 2H, CH$_2$O), δ=3.5 ppm (A B, 2H, S-CH$_2$) and δ=2.0 ppm (s, 3H, OCOCH$_3$).

EXAMPLE 9

7-[α-syn-Ethoxycarbonyl-methoximino-α-(2-amino-5-chlorothiazol-4-yl)-acetamido]-cephalosporanic acid.

Stage 1

A suspension of 17.18 g of α-syn-hydroximino-α-(2-tritylamino-thiazol-4-yl)-acetic acid in 400 ml of dry tetrahydrofuran was added to 9.52 g of potassium tert.-butylate in 80 ml of dry tetrahydrofuran. After adding 20 ml of a 4 molar solution of water in tetrahydrofuran, the mixture was stirred at room temperature for 1 hour. 6.68 g of ethyl bromoacetate in 50 ml of tetrahydrofuran were added dropwise to the violet suspension in the course of 1 hour. A further 0.95 g of potassium tert.-butylate was then added. The solution was stirred overnight.

It was concentrated to dryness, the residue was taken up in 80 ml of H$_2$O and the mixture was extracted with ethyl acetate, once at pH 7.4 and three times at pH 1.5. After drying and concentrating, the acid ethyl acetate extract gave 17.9 g of α-syn-ethoxycarbonylmethoximino-α-(2-tritylamino-thiazol-4-yl)-acetic acid with R$_F$=0.52 (glacial acetic acid/acetone=1/10).

NMR (DMSO-d$_6$): δ=7.23 ppm (s, 15H, trityl-H), δ=6.7 ppm [402 Hz] (s, 1H, thiazole-H, syn), δ=4.52 ppm [272 Hz] (s, 2H, CH$_2$CO$_2$), δ=4.12 ppm (q, 2H, CO$_2$CH$_2$CH$_3$) and δ=1.18 ppm (t, 3H, CO$_2$CH$_2$CH$_3$)

Stage 2

2.06 g of the compound obtained in Stage 1 were dissolved in 50 ml of chloroform, and 4.5 ml of a 1 molar solution of Cl$_2$ in glacial acetic acid were added at 0°. After stirring the mixture at 0° for ½ an hour, the chloroform was stripped off and the residue was slowly added to 100 ml of ice-water, whilst stirring. After stirring the mixture for ½ an hour, 1.4 g of α-syn-ethoxycarbonyl-methoximino-α-(2-trityl-amino-5-chloro-thiazol-4-yl)-acetic acid, melting point=90°–100° (decomposition), could be obtained by filtration.

R$_F$: 0.66 (butyl acetate/CHCl$_3$/85% strength HCO$_2$H=6/4/2)

NMR (DMSO-d$_6$); δ=8.93 ppm (s, broad, NH), δ=7.25 ppm (s, 15H, trityl-H), δ=4.63 ppm [278 Hz] (s, 2H, CH$_2$CO$_2$), δ=4.13 ppm (q, 2H, CO$_2$CH$_2$CH$_3$) and δ=1.15 ppm (t, 3H, CO$_2$CH$_2$CH$_3$).

Stage 3

2.75 g of the acid obtained in Stage 2, together with 0.675 g of 1-hydroxybenzotriazole, were dissolved in 50 ml of dry tetrahydrofuran, and 1.08 g of dicyclohexylcarbodiimide were added. After stirring the mixture at room temperature for one hour, 0.83 g of dicyclohexylurea was filtered off. A solution of 1.36 g of 7-aminocephalosporanic acid and 1.52 g of triethylamine in 30 ml of acetone/5 ml of H$_2$O was added to the mother liquor, whilst stirring. After stirring the mixture overnight, it was concentrated, the residue was taken up in 50 ml of ethyl acetate and the solution was extracted with H$_2$O at pH 1.8. After evaporating the ethyl acetate phase, 4.4 g of a brown-colored residue remained.

This residue was stirred in 12 ml of 75% strength HCO$_2$H at 50° for 1 hour, the mixture was extracted twice with toluene and the product phase was decolorized with 1 g of active charcoal. The light-colored formic acid solution was added dropwise to a stirred solution of 26 g of (NH$_4$)$_2$SO$_4$ in 56 ml of water. 0.8 g of 7-[α-syn-ethoxycarbonyl-methoximino-α-(2-amino-5-chloro-thiazol-4-yl)-acetamido]-cephalosporaic acid with a melting point of 175°–80° (decomposition) was thus obtained.

IR (KBr): 1,765 cm$^{-1}$ (β-lactam) and 1,725 cm$^{-1}$ (OCOCH$_3$ and —CO$_2$C$_2$H$_5$)

NMR (DMSO-d$_6$): δ=9.5 ppm (d, 1H, CONH), δ=7.22 pm (s, broad, NH$_2$), δ=5.7 ppm (2, 7-H), δ=5.1 ppm (d, 6-H), δ=4.82 ppm (A B, 2H, CH$_2$O), δ=4.65 ppm [279 Hz syn] (s, 2H, C̲H̲$_2$CO$_2$), δ=4.13 ppm (q, 2H, OC̲H̲$_2$CH$_3$), δ=3.5 ppm (d, 2, 2-H), δ=2.0 ppm (s, 3H, COCH$_3$) and δ=1.2 ppm (t, 3H, OCH$_2$C̲H̲$_3$).

We claim:

1. A compound of the formula

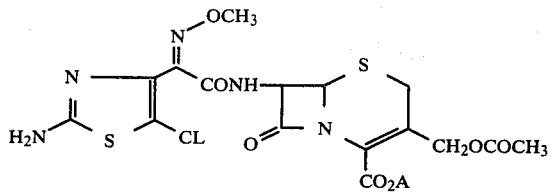

wherein A is hydrogen, a cleavable ester group, or a physiologically acceptable cation, and wherein, in the formula, =N—OCH$_3$ is present in the syn form.

2. A compound as in claim 1 wherein A is a cleavable ester group selected from the group consisting of the tert.-butyl, trimethyl silyl, benzyl, benzhydryl, trichloro ethyl, benzoyl methyl, methoxy methyl, and p-methoxy benzyl ester groups.

3. An antibacterial composition comprising an effective amount of a compound as in claim 1 in dosage form or in dosage form with a pharmaceutical carrier therefor.

4. A method for combatting a bacterial infection in a warm blooded host which comprises administering internally to said host a compound as in claim 1 in dosage form.

* * * * *